United States Patent [19]

Watson et al.

[11] 4,091,008

[45] May 23, 1978

[54] PRODUCTION OF A GAS RICH IN METHANE

[75] Inventors: Alan Watson, Ottobrunn; Peter Hohmann, Munich; Herbert Schmid, Raitenhaslach-Haslach; Helmut Schneider, Grunwald, all of Germany

[73] Assignee: Linde Aktiengesellschaft, Wiesbaden, Germany

[21] Appl. No.: 606,895

[22] Filed: Aug. 22, 1975

[30] Foreign Application Priority Data

Aug. 23, 1974 Germany ............................ 2440456

[51] Int. Cl.² .............................................. C07C 1/04
[52] U.S. Cl. ............................... 260/450; 260/449 M; 260/449.6 M; 48/196 A; 48/197 R
[58] Field of Search .......... 260/449 M, 450, 449.6 M; 48/196, 197

[56] References Cited

U.S. PATENT DOCUMENTS

| | | | |
|---|---|---|---|
| 2,863,527 | 12/1958 | Herbert et al. | 62/17 |
| 3,854,895 | 12/1974 | Muller | 260/449 M X |
| 3,904,389 | 9/1975 | Banquy | 260/449 M X |
| 3,922,148 | 11/1975 | Child | 260/449 M X |

OTHER PUBLICATIONS

Rudolph, Chemical Economy & Engineering Review, (1973) 5, No. 10, pp. 8–17.
Mueller et al., Hydrocarbon Processing, 1974, pp. 69–74.

*Primary Examiner*—Howard T. Mars
*Attorney, Agent, or Firm*—Millen & White

[57] ABSTRACT

In a process for the production of a methane-rich gas from a feed gas of hydrogen and carbon oxides, wherein the feed gas, after preliminary purification thereof, is warmed, then subjected to a multistage, catalytic methanization, and thereupon is subjected to a $CO_2$ separation step, the improvement which comprises conducting the preliminary purification step as well as at least a portion of the $CO_2$ separation step by a physical scrubbing process; and employing the same scrubbing agent in both of said physical scrubbing steps.

6 Claims, 1 Drawing Figure

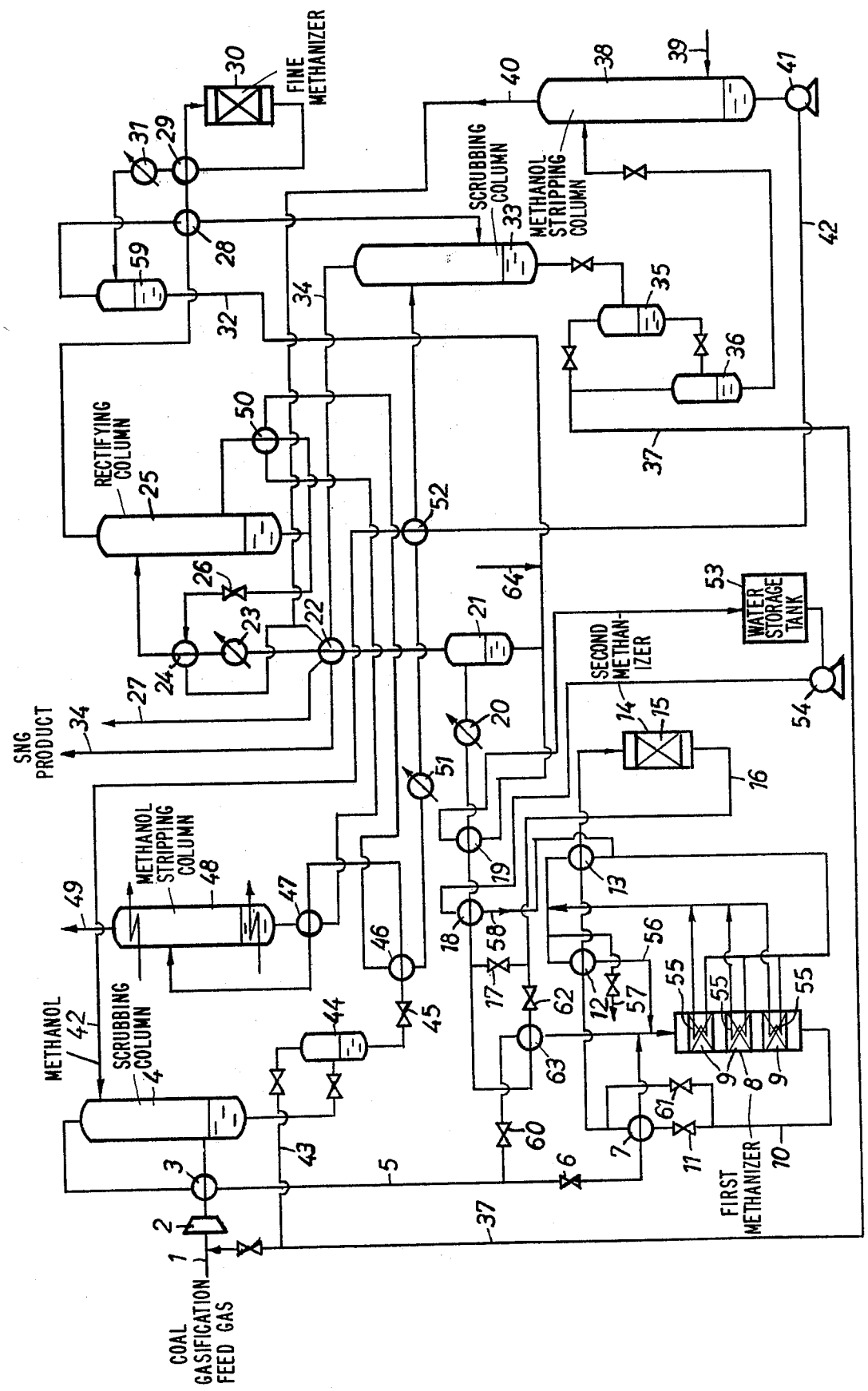

PRODUCTION OF A GAS RICH IN METHANE

BACKGROUND OF THE INVENTION

This invention relates to a process for the production of a gas rich in methane from a feed gas of hydrogen and carbon oxides, wherein the feed gas, after its preliminary purification is warmed, then subjected to a multistage catalytic methanization, and thereupon is subjected to a $CO_2$ separation.

It is old to methanize coal gasification gas consisting essentially of $CO_2$, CO, $CH_4$, and $H_2$, as well as impurities, especially sulfur compounds, with the use of a suitable catalyst. After a final $CO_2$ separation, the thus-obtained methane-rich product can be further utilized as a gas which can be substituted for natural gas (SNG). The details of such systems herein are described in the literature.

One difficulty of such a methanization process is caused by the presence of the sulfur compounds, which can lead to poisoning of the catalysts employed. To solve this problem, a preliminary step (prior to the methanization of the coal gasification gas) has been proposed to separate the sulfur compounds contained therein by means of suitable adsorbents, such as activated carbon or ZnO. Since the adsorbability of such adsorbents is, however, limited, and rather large amounts of sulfur compounds are contained in the coal gasification gas, a continuous operation is possible only with the use of several interchangeable adsorbers. This type of operation is, however, disadvantageously expensive.

SUMMARY OF THE INVENTION

An object of the present invention is to provide a simpler and less expensive system for the production of a methane-rich gas from a feed gas of carbon oxides and hydrogen.

Upon further study of the specification and appended claims, further objects and advantages of this invention will become apparent to those skilled in the art.

To attain these objects, a system is provided wherein the preliminary purification step as well as at least part of the $CO_2$ separation step is conducted by means of a physical scrubbing and by utilizing the same scrubbing agent for both steps.

The combination of the preliminary purification of the feed gas with the final $CO_2$ removal by way of the recycled scrubbing agent, normally methanol, in accordance with this invention leads to a substantial simplification of the process.

The scrubbing agent is first utilized in a first scrubbing column for scrubbing out impurities, especially sulfur compounds, from the feed gas to be methanized. By the use of the physical scrubbing step, it is possible to reduce the sulfur content of the feed gas to an extent harmless to the methanizing catalyst, e.g. below about 0.1 ppm. Thereupon, the scrubbing agent is regenerated in a stripping column and then introduced into a second scrubbing column for the final $CO_2$ removal from the methane-rich reaction product. After another regeneration by stripping with nitrogens, the scrubbing medium is recycled into the first scrubbing column. As a result, only a single scrubbing agent is used in the entire process. Advantageously, $CO_2$-laden methanol is returned into the first scrubbing column, rather than pure methanol. In this case, the heat of reaction in the first scrubbing column is minor. The operating temperatures of both scrubbing columns are suitably at the same level, below 0° C. but above the freezing point, and preferably about −10° to −35 ° C.

If the methane-rich reaction product is highly enriched with $CO_2$, e.g. above about 6 atm partial pressure, a $CO_2$ rectifying stage is advantageously disposed in front (upstream) of the final $CO_2$ scrubbing stage; in this rectifying stage, the reaction product is separated into a liquid $CO_2$ fraction and a gaseous fraction of methane, $CO_2$, hydrogen, and in some cases also CO. By conducting the rectification upstream, the load on the $CO_2$ scrubbing stage is substantially reduced, thereby requiring less scrubbing agent in total. The temperature level of the rectification corresponds to that of the $CO_2$ scrubbing stage and to the scrubbing stage employed for purifying the feed gas. The cold losses of the process are advantageously compensated for by the liquid $CO_2$ obtained in the sump of the rectifying column and/or by an additional open or closed $CO_2$ cycle.

In case the methane-rich reaction product is still relatively greatly enriched with hydrogen, e.g. above 1 molar percent, it is advantageously subjected to a further fine-methanizing step. This step is preferably conducted before the final $CO_2$ removal. By this sequence, due to the higher $CO_2$ content, the chemical equilibrium is more favorable during methanization than if the fine-methanization were conducted after the final $CO_2$ scrubbing step. Additionally, the methane-rich final product leaving the plant is obtained in an absolutely dry state. This would not be the case if the fine-methanization were conducted as the last process step.

The process of this invention is especially amenable to the methanization of a coal gasification gas. However, the process can also be utilized for the methanization of other gases containing carbon oxides and hydrogen, such as for example, oil gasification gases or refuse gasification gases. In general, the methanization of any gas of the following composition range is facilitated by the invention

| | | |
|---|---|---|
| $H_2$ | 5 – 50 | mol% |
| $N_2$ | 0 – 10 | " |
| CO | 10 – 70 | " |
| $CH_4$ | 0 – 40 | " |
| $CO_2$ | 0 – 30 | " |
| sulfur compounds | 0 – 3 | " |

Aside from methanol, other physical scrubbing agents can be employed, including, but not limited to lower monovalent alcohols, such as ethanol and propanol, multivalent alcohols, such as glycols, and ketones, such as acetone.

DESCRIPTION OF THE PREFERRED EMBODIMENTS

The attached drawing is a comprehensive schematic representation of the preferred embodiment of this invention, and is described as follows:

The feed gas to be treated, a coal gasification gas obtained during the gasification of coal and consisting by volume essentially of about 33 % $H_2$, 11 % $CO_2$, 55 % CO, 0.1 % $CH_4$, and impurities, particularly 1% sulfur compounds, is introduced into the plant via a conduit 1, compressed to the operating pressure of about 30 atmospheres in a compressor 2, cooled in a heat exchanger 3 to about −20° C, and subjected to a physical scrubbing step, using methanol as scrubbing agent, in a scrubbing column 4. The purified head product of the scrubbing column 4 is warmed in heat exchanger 3 and fed via a conduit 5, a valve 6, and a heat exchanger 7 to a first methanizing reactor 8. Accelerated by catalysts 9, preferably a Ni-based catalyst.

Chemical reactions take place within the reactor in accordance with the reaction equations $$CO + 3H_2 \rightleftharpoons CH_4 + H_2O + Q$$

$$CO_2 + 4H_2 \rightleftharpoons CH_4 + 2H_2O + Q$$

In other words, the carbon oxides contained in the feed gas are converted by chemical reaction with hydrogen into methane and water vapor, the heats of reaction liberated during these exothermic reactions being denoted by Q. The hot reaction products at a temperature of about 500° C at the bottom of the reactor 8, are thereupon passed via the steam superheater 12 and the evaporator 13 at an activating temperature about 280° C., to a second methanizing reactor 14 with a catalyst 15 which is also preferably Ni-based.

In the second methanizing reactor, almost the entire CO still present in the charge is converted essentially adiabaticly, into methane and water vapor, so that the reaction product leaving the second methanizing reactor 14 comprises substantially only about 64% $CO_2$, 34% $CH_4$, and minor amounts of about 0.8% $H_2$ and 0.1% CO (dry basis). This reaction product is withdrawn via a conduit 16 and a valve 17 and cooled to about 25° C. in heat exchangers 18 and 19 against boiler feed water and in a further cooler 20. A portion of the residual heat removed in the cooler 20 can, in certain cases, be utilized for the production of low-pressure steam. The thus-condensed steam is separated from the reaction product in a separator 21 and recycled to the feed water supply system.

The feed water to remove the heat of reaction obtained in the two methanizing reactors 8 and 14 is fed to the plant via a conduit 64, warmed in the heat exchanger 19 together with the water formed in the separators 59 and 21, and thereupon introduced into a storage tank 53. The water stored in tank 53 is compressed to a high pressure of about 60 atmospheres by means of the pump 54 and further warmed in heat exhcanger 18. A portion, about 5 to 30%, of this high-pressure water is then evaporated in the heat exchanger 13 disposed downstream of the first reactor 8, and the remainder is evaporated in the cooling coils 55 arranged in the reactor 8. A part of the high-pressure steam produced in this way is superheated in heat exchanger 12 and fed via a conduit 56 directly as process steam into the feed gas flowing to the reactor 8. The remainder is withdrawn from the plant as excess steam via a conduit 57.

In accordance with the above-described mode of operation wherein the heating of the feed gas to the activating temperature of the first reactor 8 takes place in heat exchanger 7 in heat exchange with the reaction product of reactor 8, a portion of the thus-produced heat at a high temperature level can be removed in the form of high-pressure steam exiting by way of conduit 57. The proportion of high-pressure steam fed via conduit 56 to the feed gas can be maintained at a relatively low value, e.g. about 20 to 40%, so that the heat exchangers 18, 19 and 20 connected downstream of the second reactor are sufficient to remove the residual heat.

In case the heats of reaction produced in the reactors 8 and 14 are to be released at a low temperature level, e.g. about below 400° C, the feed gas is heated to the activating temperature of the first reactor 8 in heat exchange with the reaction product of the second reactor 14 in the heat exchanger 63. In this case, the valves 6, 11, and 17 are closed, and the valves 60, 61 and 62 are opened. The amount of high-pressure steam admixed to the feed gas prior to entering the first reactor via conduit 56 corresponds exactly to the amount of steam formed in evaporators 13 and 55 and superheated in the superheater 12. The entire excess heat then occurs downstream of the second reactor 14 and can be utilized in heat exchangers 19 and 20 for the production of low-pressure steam. The advantage of this modification of the process is that less heat needs to be removed in the first reactor 8, whereby smaller and less expensive apparatus can be employed.

The gaseous fraction obtained in the separator 21, consisting essentially only of $CO_2$, $CH_4$, and minor amounts of $H_2$ and CO, is further cooled in heat exchangers 22 and 24, as well as an interposed cooler 23 to about $-50°$ C. and thereupon is subjected to a $CO_2$ rectification in the rectifying column 25. The liquid sump product of column 25, almost pure $CO_2$, is expanded in a valve 26, evaporated and warmed in heat exchangers 24 and 22 against the gaseous mixture to be rectified, and withdrawn as the product from the plant via a conduit 27.

In the head of column 25, a fraction is obtained containing, in addition to $CH_4$, also about 37% $CO_2$ and minor amounts of about 1.4% $H_2$ and 0.1% CO. This fraction is warmed in heat exchangers 28 and 29 to the activating temperature, e.g. about 280° C. of a fine-methanization reactor 30 wherein almost the entire amount of hydrogen still contained in the feed gas is converted into $CH_4$ and steam. The reaction product of the reactor 30 is cooled in the heat exchangers 28 and 29 and in a water cooler 31 and subjected to a water separating step in a separator 59. The thus-produced water is recycled via a conduit 32 to the feed water supply system.

The gaseous fraction from the separator 59, consisting essentially only of $CH_4$, $CO_2$, and traces of $H_2$ and CO is cooled in heat exchanger 28 to about $-30°$ C. and then subjected to a physical $CO_2$ scrubbing step in a scrubbing column 33 with the use of methanol as the scrubbing agent. In the head of the scrubbing column 33, almost pure methane, e.g., purity about 97% is obtained which, after being heated in heat exchanger 22, is withdrawn via a conduit 34 from the plant as the final product. This product can be further employed, for example, as substitute natural gas (SNG).

In the methanol obtained in the sump of the scrubbing column 33, methane and minor amounts of $H_2$ and CO are dissolved, in addition to $CO_2$. To increase the methane yield, the methanol at a pressure of about 26 atmospheres is then subjected to an intermediate expansion to about 5 atmospheres into the two separators 35 and 36. During this step, the major portion of the dissolved methane is driven out and again admixed, via a conduit 37, to the feed gas introduced into the plant via conduit 1.

The $CO_2$-laden methanol obtained in separators 35 and 36 is further expanded to about 2.5 atmospheres into a stripping column 38 and here subjected to a stripping step with nitrogen fed via conduit 39. The head product of the stripping column withdrawn via a conduit 40 contains only nitrogen, $CO_2$, and a minor proportion of methane. This head product is admixed, upstream of the heat exchanger 22, to the sump product of the CO₂ rectifying column 25. In the sump of the stripping column 38, methanol preliminarily absorbed with about 3 to 8% by weight $CO_2$ is obtained which is pumped by means of pump 41 via conduit 42 into the scrubbing column 4 and is now utilized as a scrubbing agent for the preliminary purification of the feed gas, especially for the separation of the sulfur compounds.

The sump product of the scrubbing column 4 is first subjected to intermediate expansion to about 10 atmospheres into a separator 44 to drive out volatile components which are again admixed to the feed gas entering via conduit 1 by way of a conduit 43, and thereupon, after further expansion in valve 45 to about 4 atmospheres and warming in the heat exchangers 46 and 47 to about 80° C, is introduced into a stripping column 48. In the head of column 48, a fraction is obtained consisting essentially of $CO_2$ and sulfur compounds, such as $H_2S$; this fraction is withdrawn via a conduit 49. This fraction can be fed to a device for the production of pure sulfur. In case the sulfur content of this fraction is too low, this content can be enriched to a desired degree by using a rewashing column between the expansion valve 45 and the heat exchanger 46.

The sump product of column 48, consisting essentially of methanol, is recycled as scrubbing agent into the $CO_2$ scrubbing column 33 after being cooled in the heat exchangers 47, 50, 46, 51 and 52 to about −60° C. Thus, a special advantage is attained by the utilization of only a single scrubbing agent for the entire process.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of a methane-rich gas from a feed gas containing carbon monoxide and hydrogen wherein the feed gas, after preliminary purification thereof is warmed, then subjected to a multi-stage, catalytic methanization in the presence of steam, to obtain a methane-rich gas having a $CO_2$ partial pressure above 6 atmospheres which thereupon is subjected to carbon dioxide separation the improvement which comprises separating the carbon dioxide first by rectification and finally by physical scrubbing and wherein the preliminary purification is conducted as a physical scrubbing step, the scrubbing liquid being the same as in the final carbon dioxide separation step.

2. A process according to claim 1, wherein a fine-methanization is conducted between the $CO_2$ rectification and the $CO_2$ scrubbing steps.

3. A process according to claim 2, wherein the physical scrubbing agent is methanol.

4. A process according to claim 1, wherein the physical scrubbing agent is methanol.

5. A process according to claim 1, wherein the loaded scrubbing liquid from the $CO_2$ separation step is regenerated to remove a portion of dissolved carbon dioxide and recycled to said preliminary purification step, and the loaded solvent from the preliminary purification step is completely regenerated, and then recycled to said $CO_2$ separation step.

6. A process according to claim 5, wherein the physical scrubbing agent is methanol.

* * * * *